United States Patent [19]

Wallshein

[11] 4,054,996
[45] Oct. 25, 1977

[54] ORTHODONTIC APPLIANCE HAVING REPLACEABLE TOOTH ENGAGING MEMBER

[76] Inventor: Melvin Wallshein, 8645 Bay Parkway, Brooklyn, N.Y. 11214

[21] Appl. No.: 708,305

[22] Filed: July 26, 1976

[51] Int. Cl.² .............................................. A61C 7/00
[52] U.S. Cl. .................................................... 32/14 B
[58] Field of Search ............................. 32/14 B, 14 E

[56] References Cited
U.S. PATENT DOCUMENTS 2,266,860  12/1941  Griesinger ........................... 32/14 E

*Primary Examiner*—Robert Peshock
*Attorney, Agent, or Firm*—Flynn & Frishauf

[57] ABSTRACT

An orthodontic appliance, such as a plate, has means defining at least one opening therein, the opening having a resilient and deformable inner surface portion, and an elongated wire-type member having at least one end which is removably insertable in the opening of the first member. The elongated member has an engaging means for resiliently deforming the inner surface portion of the opening for lockingly and non-rotatably engaging the elongated member in the opening. When the plate is of a relatively hard material, a sleeve of resilient, deformable material is used to define the opening for receiving the elongated member.

30 Claims, 20 Drawing Figures

ORTHODONTIC APPLIANCE HAVING REPLACEABLE TOOTH ENGAGING MEMBER

The present invention relates to orthodontic appliances, and more particularly to orthodontic appliances having an elongated wire-type member which is removably insertable in an opening of an orthodontic appliance, such as a removable plate.

The invention is still more particularly applicable to removable dental plates having wire-type members protruding therefrom for performing either a holding function in the mouth or an orthodontic tooth moving function. In such orthodontic appliances, the wire-type elongated members protruding therefrom often break off, especially at around the point at which they extend out from the appliance, such as a plate. Heretofore, in order to repair such a plate, it has been necessary to remove the plate from the wearer's mouth, take a new set of impressions, have the plate repaired, and then reinstall the plate at a subsequent visit. This is a highly time-consuming operation and creates patient discomfort and inconvenience, as well as being expensive to the patient due to the fact that two visits to the orthodontist, or the like, are required to effect a repair.

It is the object of the present invention to provide an orthodontic device having a removable elongated wire-type member inserted therein, the wire-type member being removably and lockingly engaged in the appliance so as to be non-rotatable in the appliance after it is locked therein.

A further object of the present invention is to provide such an appliance which is particularly suitable for orthodontic use and wherein the elongated wire-type member is quickly and easily removable from the appliance so as to be easily replaced in a quick and inexpensive manner.

A still further object of the present invention is to provide such a device which is easily fabricated and which is particularly suitable to mass production techniques.

SUMMARY OF THE INVENTION

In accordance with the present invention, an orthodontic appliance comprised a first member adapted to be located in a mouth and in proximity to a tooth, the first member having means defining at least one opening therein. Further provided is an elongated wire-type member having at least one end removably insertable in at least one opening of the first member and including means for cooperatively coupling the elongated wire-type member to at least one tooth. The opening defining means of the first member and at least one end of the elongated member which is remote from the tooth coupling portion thereof together have releasable cooperative engaging means for lockingly and non-rotatably engaging the elongated member in the opening of the first member, whereby upon application of a removal force greater than the locking engaging force, the elongated member may be removed from the at least one opening to permit insertion of another elongated member therein, thereby enabling easy and quick replacement of a damaged elongated member without requiring additional impressions to be taken and without requiring a second visit by the patient to the orthodontist.

An important feature of the present invention is that the elongated member is retained in the first member with a predetermined locking force in the axial direction so that the elongated member is not easily pulled out of the first member, and with a predetermined non-rotatably engaging force so that the elongated member retains its relative orientation with respect to the first member, regardless of normal torquing forces applied thereto in the mouth.

In accordance with another feature of the invention, a sleeve of resilient, deformable material is embedded in the first member and is used to form the opening of the first member. This arrangement is especially advantageous when the first member is made of a relatively hard material, in which case the sleeve is made of a material which is resiliently deformable by the engaging means of the elongated member.

BRIEF DESCRIPTION OF THE DRAWINGS

FIG. 5 is an enlarged fragmentary sectional view of a modification of the arrangement of FIGS. 4 and 4a;

DETAILED DESCRIPTION OF PREFERRED EMBODIMENTS

Figure 1:
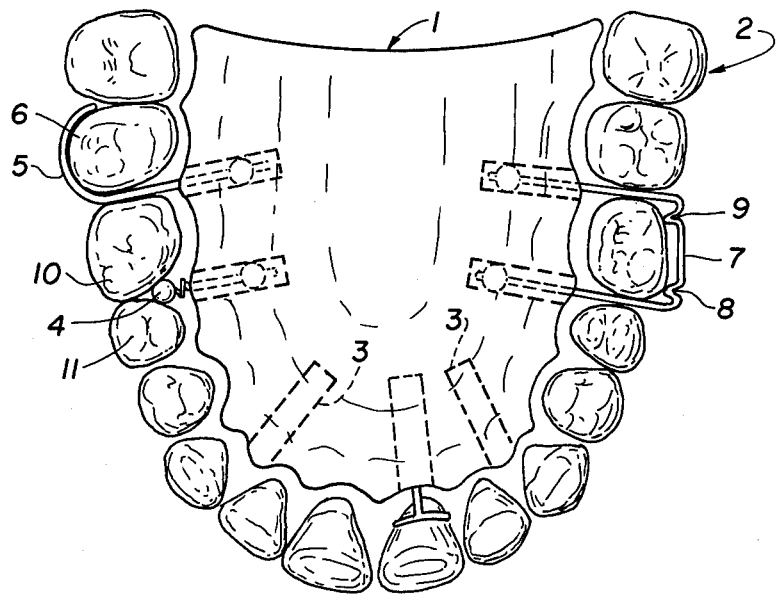
FIG. 1 is a bottom view of a dental plate oriented with respect to upper teeth, showing elongated members removably recurred thereto for applying holding and/or orthodontic forces to teeth.

Referring to FIG. 1, a removable dental plate 1, frequently utilized as a retaining device, is shown positioned lingually or palatally of the arch of a set of upper teeth 2. The removable plate 1 typically is comprised of a plastic or acrylic member which has an external peripheral portion which may be configured in the general arch-shape of the set of teeth 2. In its normal position, the plate 1 is adjacent to the palate (not shown) of the mouth. Such removable plates require securing means which prevent the appliances from moving away from the palate and falling out of the mouth by becoming disengaged from the set of teeth. Thus, clasps in the form of metal projections that fit around teeth and resist dislodging forces are generally utilized to maintain the dentures in position. Alternatively, or in addition to the conventional clasps, retaining members as shown in my earlier U.S. Pat. No. 3,827,146 may be used with the present invention. Still further, in connection with such removable plates 1, there is often required elongated members for applying orthodontic tooth-moving forces to one or more teeth, the elongated members being mounted in the plate. Still further, in accordance with the present invention, extra retaining holes or bores 3 can be provided in the plate for future use by the orthodontist if the need arises. Such additional bores 3 may be provided anywhere on the plate, the positions being shown in FIG. 1 being merely exemplary.

Figure 14:
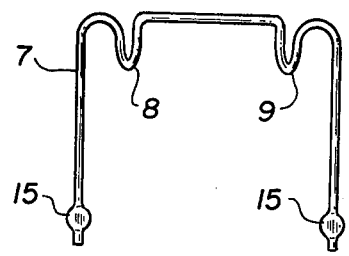
FIG. 14 illustrates a clasp for use in the present invention.

FIG. 1 shows by way of example a typical retaining device 4 bearing against a tooth 10 and which generally functions as described in my earlier U.S. Pat. No. 3,827,146. A clasp-type elongated device 5 is shown hooked around a tooth 6 for use in retaining the plate 1 in position. Another clasp member 7, removably attached to the plate 1 is shown in greater detail in FIG. 14. The clasp 7 has bent down portions 8, 9 to engage undercuts of a tooth. These devices can be used together, alone or in multiplicity, with or without other members, as desired.

Figure 2:
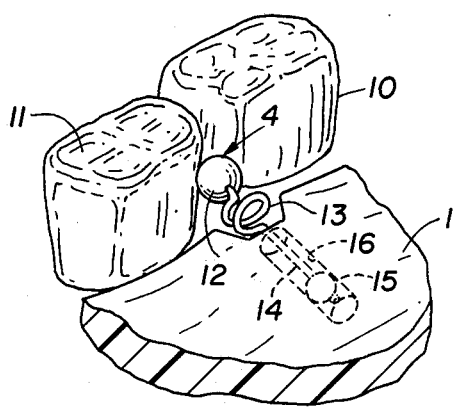
FIG. 2 is a partial perspective view of the arrangement of FIG. 1 on an enlarged scale.

FIG. 2 illustrates the retaining device of FIG. 1 in greater detail and illustrates a first technique for connecting same to the plate 1 in accordance with the present invention. A ball clasp 12 is connected at the end of a coil spring 13 which in turn is an extension of an elongated member 14. The elongated member 14 has one or more bulged portions 15 near the end thereof, which bulged portions 15 may be formed, for example, by striking the elongated member 14 with a hammer, or the like. The opening or bore 16 in the plate 1 is dimensioned so that it is undersized relative to the largest dimension of the bulged portion 15 so that when the elongated portion 14 is inserted in the opening 16, an interference fit exists. The material of the plate 1 is generally plastic material and is preferably resilient relative to the material from which the elongated member 14 is fabricated. Elongated member 14 is preferably metal. Thus, when elongated member 14 is forcedly inserted into the opening 16, the bulged portion 15 will deform the material of the plate 1 and the elongated member will be axially locked in the opening or bore 16 and will also be non-rotatably locked therein. The relative dimensions between the opening 16 and the bulged portion 15 are such that the retaining force holding the elongated member 14 within the opening or bore 16 is sufficient to prevent pulling out of the elongated member 14 or twisting thereof due to normal forces applied thereto by interaction with the teeth or intermediary appliances.

Figure 3:
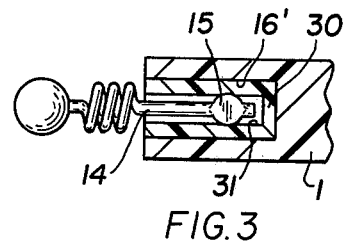
FIG. 3 is an enlarged fragmentary sectional view of a modification of the arrangement of FIG. 2.

In many instances, the plate 1 is made of a relatively hard and generally unyielding material, such as a hard acrylic material. Therefore, the bulged portion 15 of the elongated member 14 will not properly be anchored within the opening of the plate 1. FIG. 3 shows a modification of the embodiment of FIG. 5, in an enlarged partial sectional view, wherein sleeve or liner 30 of relatively soft material, such as a plastic material, is located within opening 16' of plate 1. The liner or sleeve 30 has an internal elongated opening 31 which receives the elongated member 14. The material of the liner 30 is sufficiently yieldable to be deformed upon insertion of the bulged portion 15 of the elongated member so that the elongated member 14 is anchored in the liner 30 against rotation and axial movement relative to liner 30. Liner 30 may be secured to plate 1 either by means of an adhesive or it may be molded directly into plate 1 during fabrication of plate 1. Liner 30 may be provided with irregular outer surface portions, projections, bulges, or the like, so that it is more securely and non-rotatably anchored in the plate 1. If desired, the liner or sleeve 30 may be made removable from the plate 1 upon application of a very large removal force which greatly exceeds the forces which could be expected to be put thereon when in the mouth of a patient.

Figure 15:
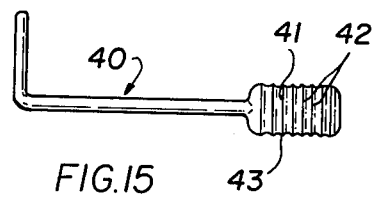
FIGS. 15-17 illustrate the modifications of the embodiment of FIGS. 1-3.

FIG. 15 illustrates a modification of the elongated member of FIGS. 1–3. In FIG. 15, the elongated member 40 has a flattened end 41 which is flattened, for example, by impacting, pounding, or the like. The end portion 41 is also formed with serrations, protrusions or roughened portions 42 which may be formed in the same step as the impacting or pounding with a suitable die, or the like. Additionally, during the impacting or pounding step, side serrations or roughened portions 43, may be produced, as desired. The serrations 42 and side serrations 43 aid in deforming and gripping the plate opening within which the elongated member is inserted or the sleeve opening within which the elongated member is inserted.

Figure 16:
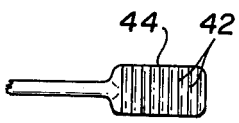
Figure 17:

FIG. 16 illustrates an embodiment similar to FIG. 15, but without the side serrations 43. FIG. 17 is a side view of the embodiment of FIG. 16 and more clearly illustrates the serrations or raised or roughened portions 42 which may be formed on one or both surfaces of the end portions 44 of the elongated member. FIGS. 16 and 17 are fragmentary views and the working end of the elongated member is not shown.

Figure 18:
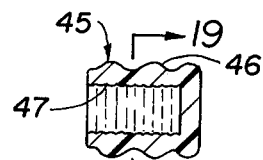
FIGS. 18 and 19 illustrate a sleeve particularly adaptable for use with the members of FIGS. 15-17.
Figure 19:
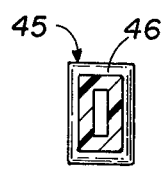

FIG. 18 is a cross-sectional view of a sleeve for use with the elongated members of FIGS. 15–17. FIG. 19 is a cross-sectional view of FIG. 18 taken along the lines 19–19. The sleeve of FIGS. 18 and 19 could also be used with other embodiments of the invention, for example those shown in FIGS. 1 and 9. The sleeve 45 is made of a soft material, for example an elastomeric material and has an undulated outer surface 46. The undulations 46 are to provide better anchoring of the sleeve in the plate 1 which is molded therearound. The inner surface 47 of the sleeve 45 is preferably generally rectangular in shape so as to more snugly receive the end portions of the elongated members illustrated in FIGS. 15–17. The inner surface 47 may be roughened, serrated, or undulated, as desired, in order to improve the retention characteristics of the elongated members inserted therein. As should be apparent, the elongated members of FIGS. 15–17 may be inserted at various depths in the opening 47 thereby providing a wide adjustability for various applications. The undulations 46 may be provided all around the sleeve 45, as indicated in FIG. 19.

Figures 4, 4A:
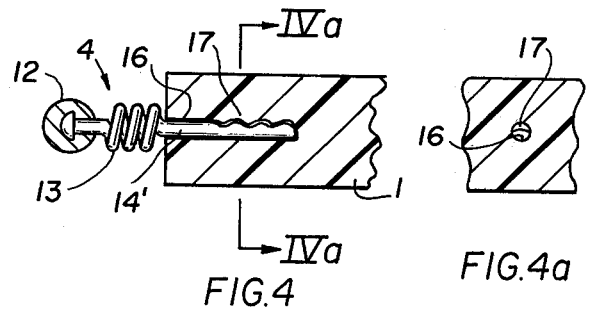
FIGS. 4 and 4a are fragmentary sectional views of a further modification of the arrangement in FIG. 2.

FIG. 4 illustrates a further modification of a retaining means. In FIG. 4 the opening or bore 16 of the plate 1 has a serrated portion 17, the serrations 17 being preferably only over a portion of the internal periphery of a transverse cross-section of the bore 16, as shown, for example, in FIG. 4a. The elongated member 14' in FIG. 4 is also serrated at at least an end portion thereof, the serrations of elongated member 14' being also only over a portion of the transverse cross-sectional periphery thereof. The serrations of the elongated member 14' and the serrations 17 and opening 16 are dimensioned so as to provide an appropriate interference fit so that upon insertion of elongated member 14 in the opening 16, the elongated member 14' is retained in the opening 16 against axial as well as rotary movement thereof. The axial engagement is provided by interengagement of the serrations and the rotational movement is prevented due to the fact that the serrations are provided only over a portion of the periphery of the various members. The serrations are suitably designed so that upon application of a suitable removal force, for example if the coil spring 13 breaks off from the elongated member 14, the elongated member 14' may be removed for replacement. It is preferably of a material which is resilient enough to yield or be deformed upon insertion of the serrated portion of the elongated member into the opening thereof.

Figure 5:
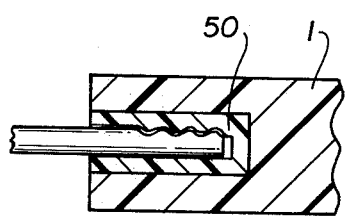

In instances where the plate 1 is of an unyielding material, or of a material which does not sufficiently yield upon insertion of the interfering fit portions of the elongated member, a sleeve or liner 50, shown in FIG. 5, having a similar configuration to the opening 16 in FIG. 4, may be provided in the plate 1.

While the arrangement of FIGS. 2-5 utilize ball clasps, the coil spring and ball clasp members may be replaced by clasps such as the circumferential clasp 5 of FIG. 1, or any other suitable device used in orthodontics in conjunction with dental plates.

Figure 6:
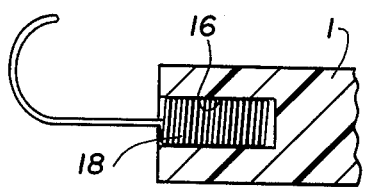
FIGS. 6 and 7 are fragmentary sectional views showing further modifications of the present invention.

FIG. 6 illustrates a further modified form of the invention wherein the opening or bore 16 in the plate 1 has inserted therein an elongated member 18 which is formed as a tightly wound coil which is other than round in the cross-sectional direction of the bore 16. The bore 16 is also other than round in cross-section and is dimensioned so as to provide a yielding interference fit with the coil spring portion 18. When the coil spring portion 18 is inserted in the bore 16, the interference fit is such as to prevent rotation of the coil spring within the bore 16 and the coil spring 18 is dimensioned so as to be yieldingly press fit within the bore 16 that it is restrained therein even under application of forces in the mouth. If the material of plate 1 is not sufficiently resilient or yielding, a sleeve of resilient material may be used as shown in FIGS. 3 and 5.

If the material of plate 1 is soft, both the bore 16 and the coil 18 could be round, the soft plate material yieldingly deforming around coil to lock same therein. Also, the coil 18 could be oval and the bore 16 round with a funnel-shaped opening to accept the oval coil, the opening 16 being yieldingly deformed to accept the interferingly fitting oval coil 18.

Figure 7:
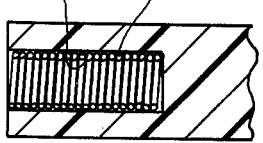

FIG. 7 illustrates a further modification wherein the bore 16 has a cylindrical coil 19 located therein, the coil 19 either being inserted therein after manufacture of the plate or being processed in the plate during manufacture, as desired. The elongated member for insertion in the embodiment of FIG. 5 could be any one of the elongated members shown in FIGS. 2-6, provided a yielding interference fit exists between the members. In a preferred embodiment, the coil 19 has a round cross-section and the elongated member comprises a member, such as shown in FIGS. 2-5, which has bulges or serrations, or projections which deform the coil to get wedged in the coil 19 so that a tight and non-rotatable fit is provided. The wedging action could be by deformation or movement of the coil 19 in the bore 16 or by wedging of serrations and/or bulges 15 between adjacent turns of the coil 19. Alternatively, a non-circular coil member 19 could be provided and a serrated elongated member 14' could be provided, the serrated portion being also oval and either being over part of the periphery of elongated member 14 or being completely therearound.

Figure 8:
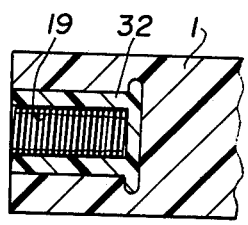
FIG. 8 is an enlarged fragmentary sectional view of a modification of the arrangement of FIG. 7.

In the event that the plate 1 is of a material which is not sufficiently yieldable, the coil 19 could be provided in an insert or sleeve 32 as shown in FIG. 8. In this arrangement, the spring 19 will be freer to yield or flex and to thereby deform the sleeve 32, to more positively engage an elongated member, such as the elongated members shown in FIGS. 2-5.

The embodiment of FIG. 8 may be fabricated with the sleeve 32 being formed of a very soft wax layer or other soft layer over the coil 19 to permit yielding or flexing of the coil due to the interfering fit of the bulges, serrations, or the like, of the elongated member inserted therein. By providing a wax or very soft layer over the coil 19, the coil 19 may be advantageously processed into the plate 1 in a simple and expedient manner, without requiring specially designed sleeves 32, or the like.

Still further, the coil 19 may be fabricated of a plastic material, instead of metal, which in and of itself may provide sufficient yieldability and deformability to engage an elongated member inserted in the central opening thereof. In the embodiments of FIGS. 7 and 8, it should be clear that the coils 19 are non-rotatably inserted in the plate 1 or in an associated sleeve 32.

A further embodiment is a modification of FIG. 4 wherein the opening 16 is serrated around the complete internal periphery thereof, the internal periphery being generally oval in shape. In this instance, the elongated member 14' could also be oval or non-circular and can be provided with serrations completely therearound so as to provide the proper interengagement to prevent axial removal except under high removal force and to prevent rotation relative to the plate 1. Also the opening 16 could be round with serrations all around and the inner surface thereof being of yielding and deformable material.

Figure 9:
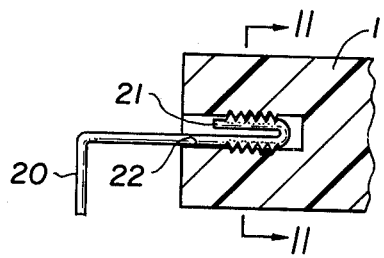
FIGS. 9-12 are fragmentary sectional views of further embodiments of the present invention.
Figure 10:
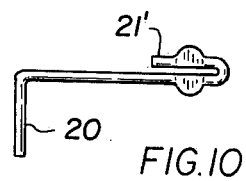
Figure 11:
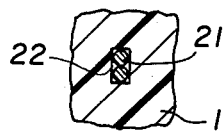
Figure 12:
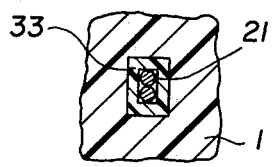

FIG. 9 shows a still further modified embodiment of the invention wherein a clasp 20 has an end portion 21 bent over on itself and which is removably engageable in an opening 22 of the plate 1. The bent over portion 21 of the clasp 20 is serrated (or bulged as shown in FIG. 10) to provide a yielding interfering fit in the opening 22. The opening 22 is oval or generally rectangular as shown in FIG. 11 to non-rotatably retain clasp 20. If the plate 1 is not sufficiently resilient or yieldable, a sleeve or insert 33 of softer material could be used as shown in FIG. 12. In FIGS. 9 and 10 the bent over portion 21 may be separated from the main part of clasp 20 to additionally provide spring action to enhance engagement with the plate or sleeve.

Figure 13:
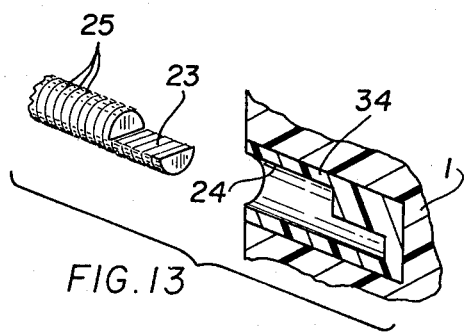
FIG. 13 is a fragmentary sectional view of a still further modification of the present invention.

FIG. 13 illustrates a still further modified form of the invention wherein the end of a clasp, spring, or the like, has a flattened portion 23 which is insertable into a matingly shaped opening 24 in a sleeve 34 which is in plate 1. The flat portion 23 maintains the non-rotatability of the elongated member relative to the plate 1 (and sleeve 34) and is further provided with, for example, serrations, ridges, or the like 25 which are over-dimensioned so as to grip the relatively resilient material of the sleeve 34 upon insertion into the opening 24. The ridges 25 may be on the flat portion 23 as well as, or instead of, over the remaining portion of the elongated member.

It should be clear that wherever the serrations are provided as described above, ribs, or other members performing similar or equivalent functions could be used.

A plate according to the present invention can be fabricated with member retaining means therein, or the various elongated engaging members can be processed into the plate during manufacture when the material of the plate is sufficiently resilient or yieldable. For example, the elongated member having the flat portion 23 and ribs 25 could be processed into the plate 1 during manufacture of the plate 1 so as to conveniently provide the corresponding mating flat portion in the plate 1 and so as to provide engagement portions for the ribs or serrations 25. Similar considerations exist with respect to the embodiment of FIGS. 2, 4 and 9. In the embodiment of FIG. 7 the fixed coil 19 may be processed into the plate 1 during manufacture of the plate 1 so as to further insure that it will not come out of the plate 1 during use. In all these embodiments the processed in devices are readily removable for replacement by application of suitable removal forces.

While serrations were shown in the embodiment of FIG. 4, the elongated member 14' could be provided with ridges or other projections thereon which would engage an opening 16'. If the opening 16' is non-circular, for example oval, and if the cross-section of the elongated member 14' is also non-circular, and for example oval, the resulting structures will provide an interference fit against rotation of the elongated member 14' relative to the plate 1. The elongated member 14' may then be provided with ridges, serrations or other engaging projections, such as enlarged portion 15 of the FIG. 2, so as to engage the internal surface of the opening 16 to prevent axial movement of the elongated member 14' relative to the plate 1 in use.

Throughout the above description, discussion of illustrated configurations of an opening of a plate 1 are equally applicable to corresponding configurations of a soft, resilient sleeve which is mounted in the plate and performs the function of the respective discussed openings.

As should be apparent the elongated members in the various embodiments can be inserted to various depths in the plate and/or sleeves, to provide convenient adjustability. Also, the various illustrated elongated members can be used with other openings in various combinations as applicable to desired applications. Still further, any of the elongated members may be oversized relative to the bore within which it is to be received. For example an elongated member 14 of FIG. 4 may have a larger diameter than the diameter of a coil 19 of FIG. 7 so that the coil 19 is deformed into the softer material of the plate or sleeve to provide the desired interengagement.

While the invention has been described above with respect to specific embodiments, it should be clear that various modifications and alterations can be made within the scope of the appended claims.

I claim:

1. An orthodontic appliance comprising:
    a first member adapted to be located in a mouth and in proximity to a tooth, said first member having means defining at least one opening therein which opens to the interior of said first member, said opening having a resilient and deformable inner surface portion;
    an elongated wire-type member having at least one end removably insertable in said at least one opening of said first member to engage said resilient and deformable inner surface portion, and further including means for cooperatively coupling same to at least one tooth;
    said at least one end of said elongated member having a contoured releasable cooperative engaging means for resiliently deforming said resilient and deformable inner surface portion of said opening defining means so that said resilient and deformable inner surface portion substantially conforms to at least a portion of the contour of said engaging means for lockingly and non-rotatably engaging said elongated wire-type member in said opening, whereby upon application of a removal force greater than the locking engaging force, said elongated wire-type member may be removed from said at least one opening to permit insertion of another elongated wire-type member therein.

2. An orthodontic appliance according to claim 1 wherein said first member is a removable dental plate.

3. An orthodontic appliance according to claim 1 wherein said at least one opening comprises a bore.

4. An orthodontic appliance according to claim 3 wherein said bore has a resilient and deformable surface portion which cooperates with an engaging portion of said elongated member to lockingly and non-rotatably engage said elongated member.

5. An orthodontic appliance according to claim 1 wherein said elongated member has a bulged portion thereon which is adapted to be inserted into said opening, said opening being dimensioned so as to interferingly engage said bulged portion so that said inner surface of said opening is resiliently deformed by said bulged portion to provide an interference and non-rotatable engagement therebetween.

6. An orthodontic appliance according to claim 1 wherein said elongated member has a non-circular periphery and said opening is non-circular, said non-circular portion of said elongated member being non-rotatably engageable in said opening.

7. An orthodontic appliance according to claim 1 wherein said opening has serrations or the like over at least a portion of the length thereof and over at least a portion of the periphery thereof, said elongated member having serrations or the like thereon for interferingly engaging said serrations of said opening and for resiliently deforming the serrations of said opening upon insertion of said elongated member in said opening.

8. An orthodontic appliance according to claim 7 wherein said serrations of said opening are provided only over a portion of the periphery thereof, and wherein said serrations or the like of said elongated member are provided only over a portion of the periphery thereof.

9. An orthodontic appliance according to claim 1 comprising a deformable coil member in said opening and said elongated member comprises means for non-rotatably and lockingly engaging said coil member and for deforming said coil member.

10. An orthodontic appliance according to claim 9 wherein said elongated member has a coiled end portion, said coiled end portion being of different cross-sectional shape than said coiled member in said opening so as to lockingly and non-rotatably engage said coiled member in said opening.

11. An orthodontic appliance according to claim 9 comprising a soft, yieldably deformable layer interposed between said coil member and said first member.

12. An orthodontic appliance according to claim 11 wherein said soft layer comprises a wax layer.

13. An orthodontic appliance according to claim 11 wherein said soft layer comprises a layer of soft plastic material.

14. An orthodontic appliance according to claim 1 wherein said elongated member has a flat portion thereof which engages a corresponding flat portion defined by said opening defining means.

15. An orthodontic appliance according to claim 1 wherein said elongated member has an end portion bent over on itself and which is insertable in said opening of said first member.

16. An orthodontic appliance according to claim 15 wherein said bent over end portion is separated from said elongated member along at least a portion of the length of said elongated member and is resiliently movable toward said elongated member.

17. An orthodontic appliance according to claim 1 wherein said releasable cooperative engaging means comprises means responsive to only axial movement of said elongated member relative to said opening to lockingly and non-rotatably engage said elongated member in said opening.

18. An orthodontic appliance according to claim 1 wherein said means defining at least one opening in said first member comprises a sleeve of resilient deformable material which is softer than the material from which said first member is made.

19. An orthodontic appliance according to claim 18 wherein said at least one end of said elongated member is of harder material than said sleeve.

20. An orthodontic appliance according to claim 18 wherein said sleeve comprises means for non-rotatably and lockingly engaging said cooperative engaging means of said elongated member.

21. An orthodontic appliance according to claim 18 wherein said elongated member has a bulged portion thereon which is adapted to be inserted into said opening defined by said sleeve, said opening being dimensioned so as to interferingly engage said bulged portion so that said sleeve is resiliently deformed by said bulged portion to provide an interference and non-rotatable engagement therebetween.

22. An orthodontic appliance according to claim 18 wherein said sleeve has serrations or the like over at least a portion of the length of the opening defined thereby and over at least a portion of the periphery of said opening, said elongated member having serrations or the like thereon for interferingly engaging said serrations of said opening and for resiliently deforming the serrations of said opening upon insertion of said elongated member in said opening.

23. An orthodontic appliance according to claim 18 wherein said engaging means of said elongated member is engageable at a plurality of depths in said opening of said sleeve.

24. An orthodontic appliance according to claim 1 wherein said engaging means of said elongated member is engageable at a plurality of depths in said at least one opening.

25. An orthodontic appliance according to claim 1 wherein said at least one end of said elongated member is of material which is harder than the material of said opening defining means.

26. An orthodontic appliance according to claim 1 wherein said elongated member has a flat end portion which is adapted to be inserted into said opening, said flat end portion having at least one surface with serrations, or the like, thereon for resiliently deforming said inner surface of said opening.

27. An orthodontic appliance according to claim 18 wherein said sleeve comprises means on the outer surface thereof for preventing movement thereof relative to said first member.

28. A method of making an orthodontic appliance comprising:
applying a layer of a first material to a helically wound coil; and
molding a first member adapted to be located in a mouth around said layer of said helically wound coil so as to enclose said helically wound coil within said first member, said first member providing an opening to the inner portion of said elongated coil;
said first material being a material which is resiliently deformable and which is softer than the material of said molded first member.

29. A method according to claim 28 wherein said layer is a wax layer.

30. An orthodontic appliance according to claim 1 wherein said resilient and deformable inner surface portion of said opening substantially conforms to substantially the complete contour of said engaging means.

* * * * *